(12) United States Patent
Endo et al.

(10) Patent No.: US 6,596,018 B2
(45) Date of Patent: Jul. 22, 2003

(54) MATTRESS WITH BEDSORE PREVENTING FUNCTION

(75) Inventors: Tatsuo Endo, Midori-ku (JP); Mitsutoshi Ikeda, Toyoake (JP)

(73) Assignee: Sakura Alumi Co., Ltd., Nagoya (JP)

( * ) Notice: Subject to any disclaimer, the term of this patent is extended or adjusted under 35 U.S.C. 154(b) by 199 days.

(21) Appl. No.: 09/803,053

(22) Filed: Mar. 12, 2001

(65) Prior Publication Data

US 2001/0020303 A1 Sep. 13, 2001

(30) Foreign Application Priority Data

Mar. 13, 2000 (JP) ........................................ 2000-068450
Feb. 21, 2001 (JP) ........................................ 2001-045020

(51) Int. Cl.[7] ................................................. A61F 7/00
(52) U.S. Cl. ........................ 607/96; 607/100; 607/104; 5/726; 5/421
(58) Field of Search ............................ 607/96, 98, 100, 607/104, 114; 5/421–423, 632, 724–726, 652.2

(56) References Cited

FOREIGN PATENT DOCUMENTS

JP        A 02004303        1/1990

Primary Examiner—Roy D. Gibson
(74) Attorney, Agent, or Firm—Oliff & Berridge PLC

(57) ABSTRACT

A mattress suitable for medical application in hospitals etc. includes a cushion body having air permeability, an air discharger provided below the cushion body for discharging air into the cushion body, and a heat source provided below the cushion body for performing far infrared radiation into the cushion body. Both the air discharger and the heat source have flexibility.

17 Claims, 18 Drawing Sheets

MATTRESS WITH BEDSORE PREVENTING FUNCTION

BACKGROUND OF THE INVENTION

1. Field of the Invention

This invention relates generally to mattresses used with hospital beds in hospitals and more particularly, to such a mattress suitable for bedridden or immobile patients who are compelled or need to lie in bed for a long period of time.

2. Description of the Related Art

It is known that bedridden or immobile patients who are compelled or need to stay in bed for medical treatment or care have lumbago, arthralgia, or bedsore due to worsened circulation of the blood. In view of this problem, a posture of the patient lying in bed is conventionally changed periodically, or air is blown out against the patient so that the occurrence and progress of arthralgia or bedsore can be prevented. However, to change the posture of the patient and to blow air against the patient are troublesome. Moreover, the posture of the patient cannot sometimes be changed depending upon the condition of the patient or a type of disease.

A mattress with an air blowing function has been put to practical use. Since air can automatically be blown against the body of the patient lying on the mattress, the occurrence and progress of bedsore can be prevented.

SUMMARY OF THE INVENTION

An object of the present invention is to provide a mattress which can prevent occurrence and progress of lumbago and arthralgia as well as bedsore.

The present invention provides a mattress comprising a cushion body having air permeability, an air discharger provided below the cushion body, the air discharger having flexibility, for discharging air into the cushion body, and a heat source provided below the cushion body for performing far infrared radiation into the cushion body, the heat source having flexibility.

According to the above-described mattress, the skin of a person lying thereon is dried by air discharged from the air discharger. Consequently, occurrence and progress of bedsore can be prevented. Further, the circulation of the blood of a person lying on the mattress is facilitated by the far infrared radiation from the heat source. Consequently, occurrence and progress of lumbago and arthralgia can be prevented.

Furthermore, both of the air discharger and heat source have flexibility. Air is discharged from the air discharger and the far infrared radiation from the heat source can be performed even when the mattress is bent or folded. Accordingly, the mattress in accordance with the invention can be used with, for example, a bed for medical treatment with a posture adjusting mechanism.

The heat source preferably comprises a generally cloth-like heat generator made of a filament yarn further made of a synthetic resin with carbon added and a metallic yarn causing the filament yarn to generate heat by means of resistance when the filament yarn is energized. Since this construction reduces the thickness of the heat source, sleep is not disturbed even when the heat source is disposed inside the mattress.

The mattress preferably further comprises an air supply for supplying air to the air discharger, an air passage connected to the air supply and the air discharger so that air is supplied from the air supply to the air discharger therethrough, and a disinfectant supply for supplying a disinfectant component into the air supplied from the air supply so that the air discharged from the air discharger contains the disinfectant component. The occurrence and progress of bedsore can be prevented since this construction prevents pyogenic bacteria from propagation on an affected part of bedsore.

The mattress preferably further comprises an air supply for supplying air to the air discharger, an air passage connected to the air supply and the air discharger so that air is supplied from the air supply to the air discharger therethrough, and a heater provided in the middle of the air passage for heating the air flowing through the air passage. Since hot air is discharged from the air discharger, the skin of a person lying on the mattress is dried and cutaneous respiration is facilitated. Consequently, the occurrence and progress of bedsore can further be prevented.

The air discharger preferably includes an air discharger for legs, an air discharger for a waist, an air discharger for shoulders, and an air discharger for a head. In this case, the mattress preferably further comprises a controller for controlling the air dischargers for the legs, waist, shoulders, and head respectively independent of one another. Air can suitably be discharged from the dischargers according to the conditions of parts of the personal body.

The heat source preferably includes a heat source for legs and a heat source for a waist. Far infrared radiation can be concentrated on the legs and waist which are susceptible to arthralgia. In this case, the mattress preferably further comprises a controller for controlling the heat sources for the leg and waist independently of each other. Consequently, far infrared radiation from the heat source can be performed according to the conditions of the legs and waist.

BRIEF DESCRIPTION OF THE DRAWINGS

Other objects, features and advantages of the present invention will become clear upon reviewing the following description of preferred embodiments, made with reference to the accompanying drawings, in which.

DETAILED DESCRIPTION OF PREFERRED EMBODIMENTS

Figure 5:
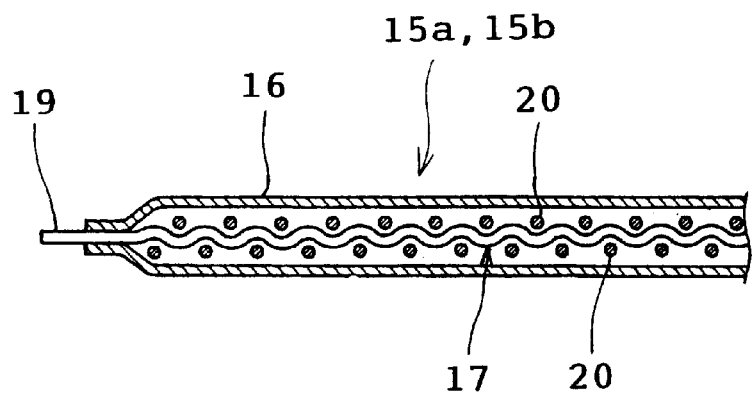
FIG. 5 is a longitudinal section of the heater.
Figure 6:
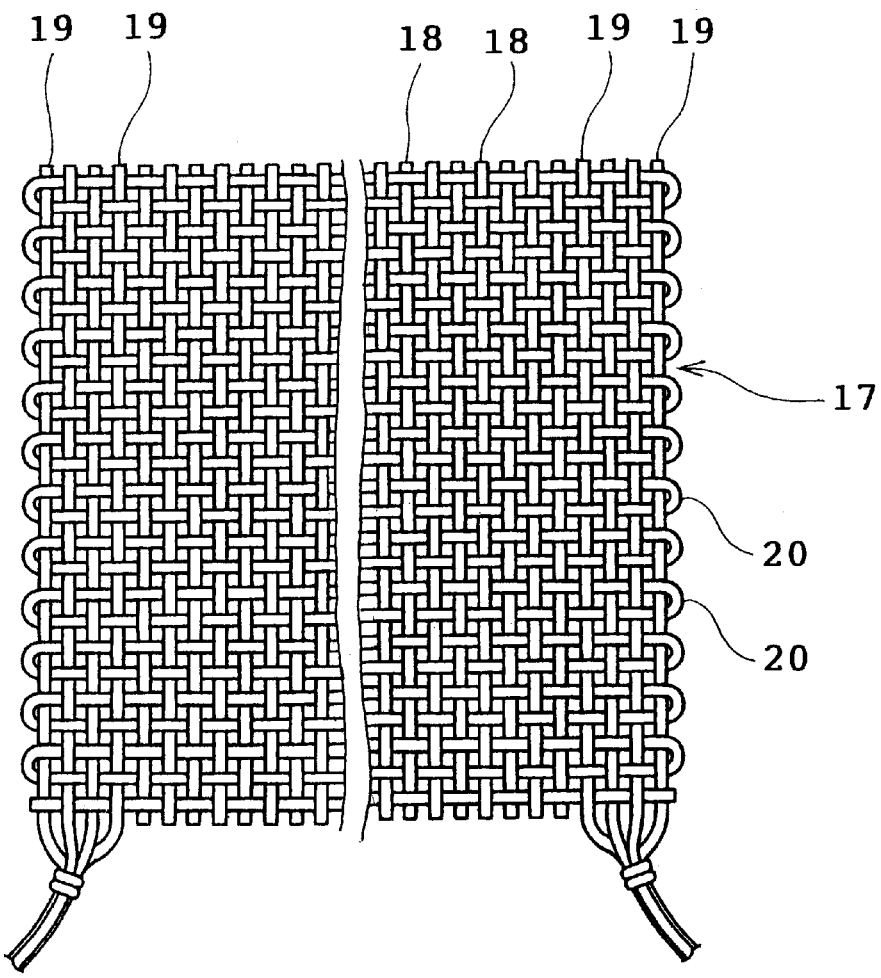
FIG. 6 is a plan view of a heating element of the heater.
Figure 7:
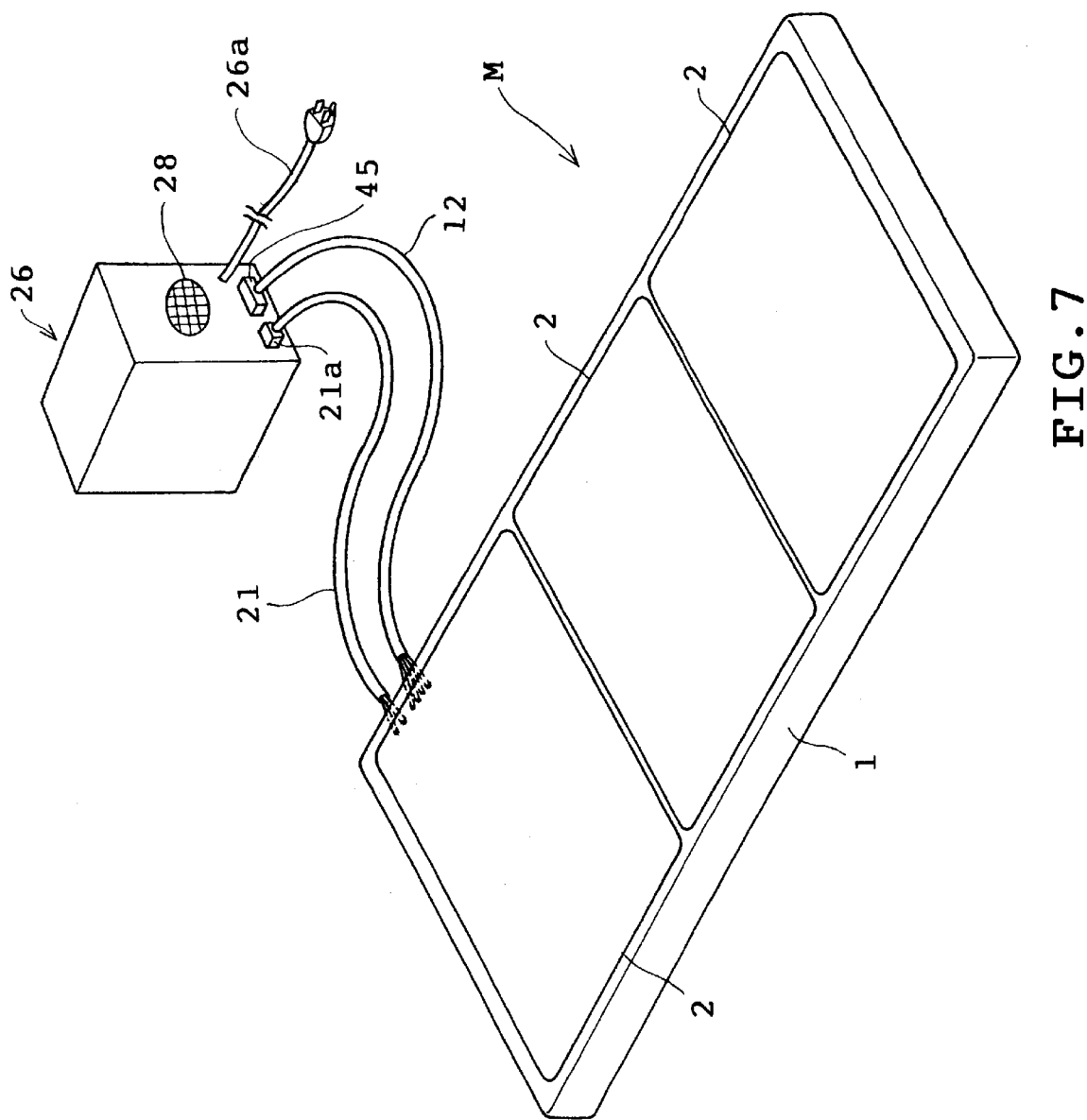
FIG. 7 is a perspective view of the mattress with a controller.

Several embodiments of the present invention will now be described. FIGS. 1 to 11 illustrate a first embodiment of the mattress in accordance with the invention. Referring first to FIG. 7, an overall mattress is shown. The mattress comprises a mattress H and a controller 26. The mattress M is formed into the shape of a generally rectangular plate and is of the overlay type. The controller 26 is made of a steel plate and formed into the shape of a generally rectangular box. The controller 26 includes an operation panel 27 (see FIG. 8) provided on the front thereof. The controller 26 further includes an air inlet 28 formed through a rear wall thereof and a power supply cord 26a extending outward through the rear wall thereof.

The mattress M will be described with reference to FIGS. 1 to 3. A person lies lengthwise on the mattress M, and his or her head is located on the right and his or her legs are located on the left as viewed in FIGS. 2 and 3. The mattress M comprises a mat cover 1 and a multilayered cushion 4 accommodated in the mat cover. The mat cover 1 is formed by sewing some pieces of cloth together into the shape of a bag. In particular, a meshed cloth 1a with high air permeability constitutes an upper side of the mat cover 1. Thus, meshes of the cloth 1a serve as air holes of the mat cover 1 although not shown in the drawings. A suitable fastener (not shown) is provided on a side of the mat cover 1 so that the cushion 4 is taken out of the cover 1 when the fastener is opened.

Three rectangular sheets 2 are attached to an upper part of the cloth 1a in parallel with each other, for example. Each sheet 2 is made of cloth with air permeability. Four sides of each sheet 2 are detachably attached to the mat cover 1 by sheet fasteners 3 (commercially available under the name of "magic tape"). Accordingly, when becoming dirty, one or more sheets 2 are detached to be washed. The cushion 4 comprises a base mat 5, base sheet 6, protecting cushion 7 and cushion body 23 stacked sequentially in this order. A plurality of, for example, four balloons 8 to 11 are fixed between the protecting cushion 7 and the cushion body 23. In FIG. 1, the protecting cushion 7 and the cushion body 23 are spaced from each other by a thickness of each balloon 8 to 11 for the sake of easy understanding although the protecting cushion 7 and the cushion body 23 are partially in contact with each other.

Figure 4:
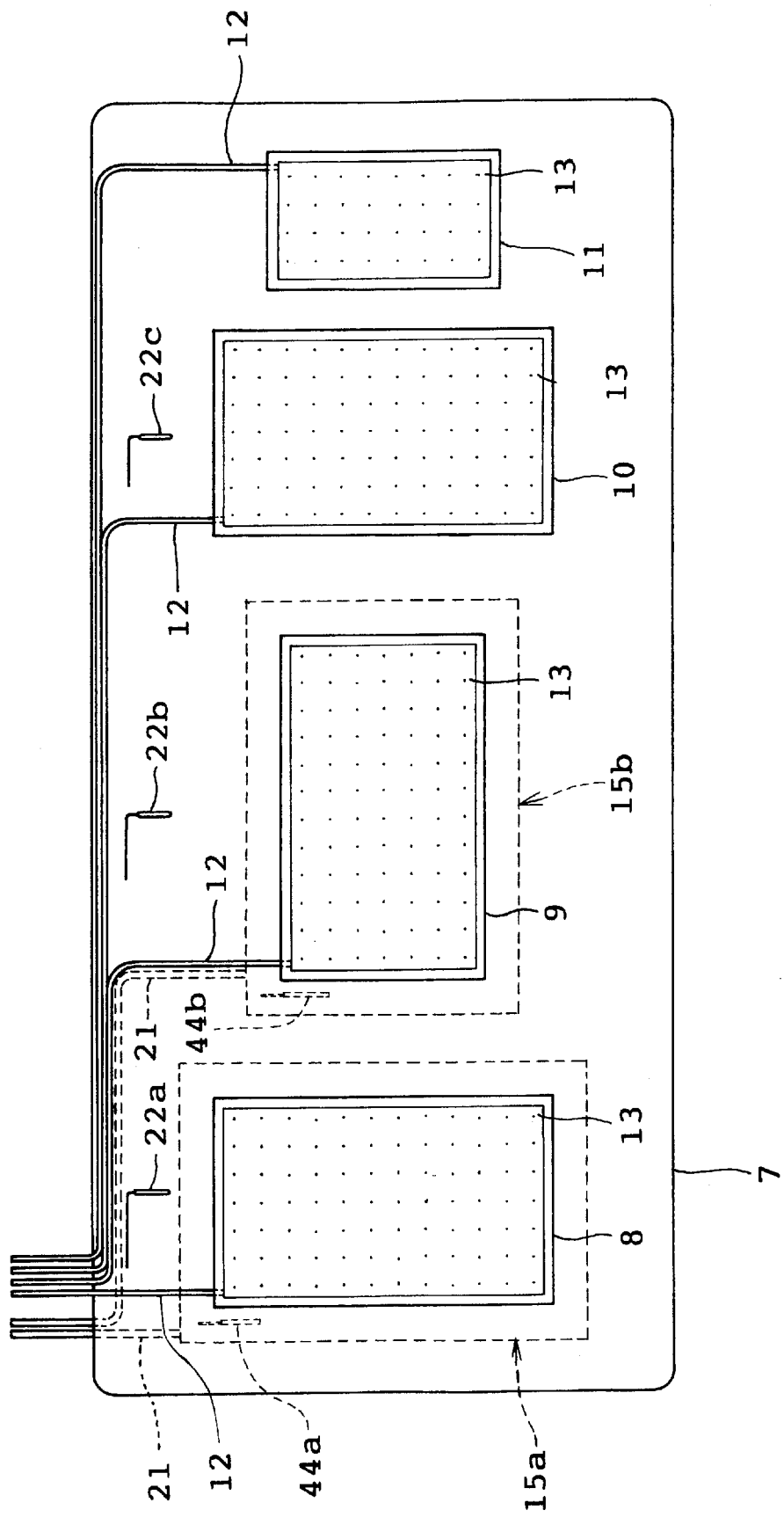
FIG. 4 illustrates arrangement of balloons and beaters on a protecting cushion.

The base mat 5 is made from a synthetic resin such as urethane foam. The base sheet 6 is placed on the base mat 5 and is made from a synthetic resin having a flexibility lower than the base mat 5. The balloons 8 to 11 serve as air dischargers respectively. Each balloon is made by welding two polyvinyl chloride sheets together into the shape of a bag. Each balloon 8 to 11 has a number of small discharge holes 13 formed through an upper face thereof. The balloons 8 to 11 are disposed on the mattress M so as to correspond to the legs, waist, shoulders and head respectively as shown in FIG. 4. Each balloon has a generally rectangular shape. Temperature sensors 22a to 22d are disposed near the balloons 8 to 11 between the protecting cushion 7 and the cushion body 23 respectively. Each temperature sensor 22a to 22d comprises a thermistor, for example and detects an ambient temperature near the corresponding balloon 8 to 11.

The protecting cushion 7 is made by bonding peripheral portions of two pieces of cushion material together into the shape of a bag as shown in FIGS. 1 to 4. A cover 14 made from a synthetic resin such as vinyl leather with waterproof is bonded to an outer surface of the protecting cushion 7. A plurality of, for example, two heaters 15a and 15b are enclosed in the protecting cushion 7. The heaters 15a and 15b are disposed below the balloon 8 for the legs and the balloon 9 for the waist respectively. Each heater 15a and 15b comprises a heater cover 16 and a cloth-like heating element 17 serving as a heat source and enclosed in the heater cover 16 as shown in FIGS. 5 and 6. Temperature sensors 44a and 44b (see FIG. 4) are provided in the heater covers 16 for sensing surface temperatures of the heating elements 17 respectively. Each temperature sensor 44a and 44b comprises a thermistor, for example.

Each heater cover 16 is formed by welding an electrically insulating sheet made from vinyl chloride into the shape of a bag. Each heating element 17 has substantially the same construction as described in Japanese Patent No. 1661444 granted on the assignee of this application. More specifically, each heating element 17 is formed by weaving a synthetic resin fiber 18 such as polyethylene, copper yarn 19 and filament yarn 20 into a flat shape. The filament yarn 20 is formed by intertwisting a plurality of pieces of filament each of which pieces consists of 72 to 70% polyethylene resin with a predetermined heat resistance and 28 to 30% scaly carbon by weight. The synthetic resin fiber 18 constitutes central warp of the heating element 17. The copper yarn 19 constitutes warp at both ends of the heating element 17. The filament yarn 20 constitutes overall weft. Power is supplied through the power supply cord 21 (see FIGS. 3 and 7) to the copper yarn 17. The connector 21a at the end of the cord 21 is detachably connected to a connector (not shown) in the rear of the controller 26. When power is supplied to the copper yarn 19, the filament yarn 20 is energized such that the filament yarn generates heat by resistance, thereby emitting far infrared radiation.

Figure 1:
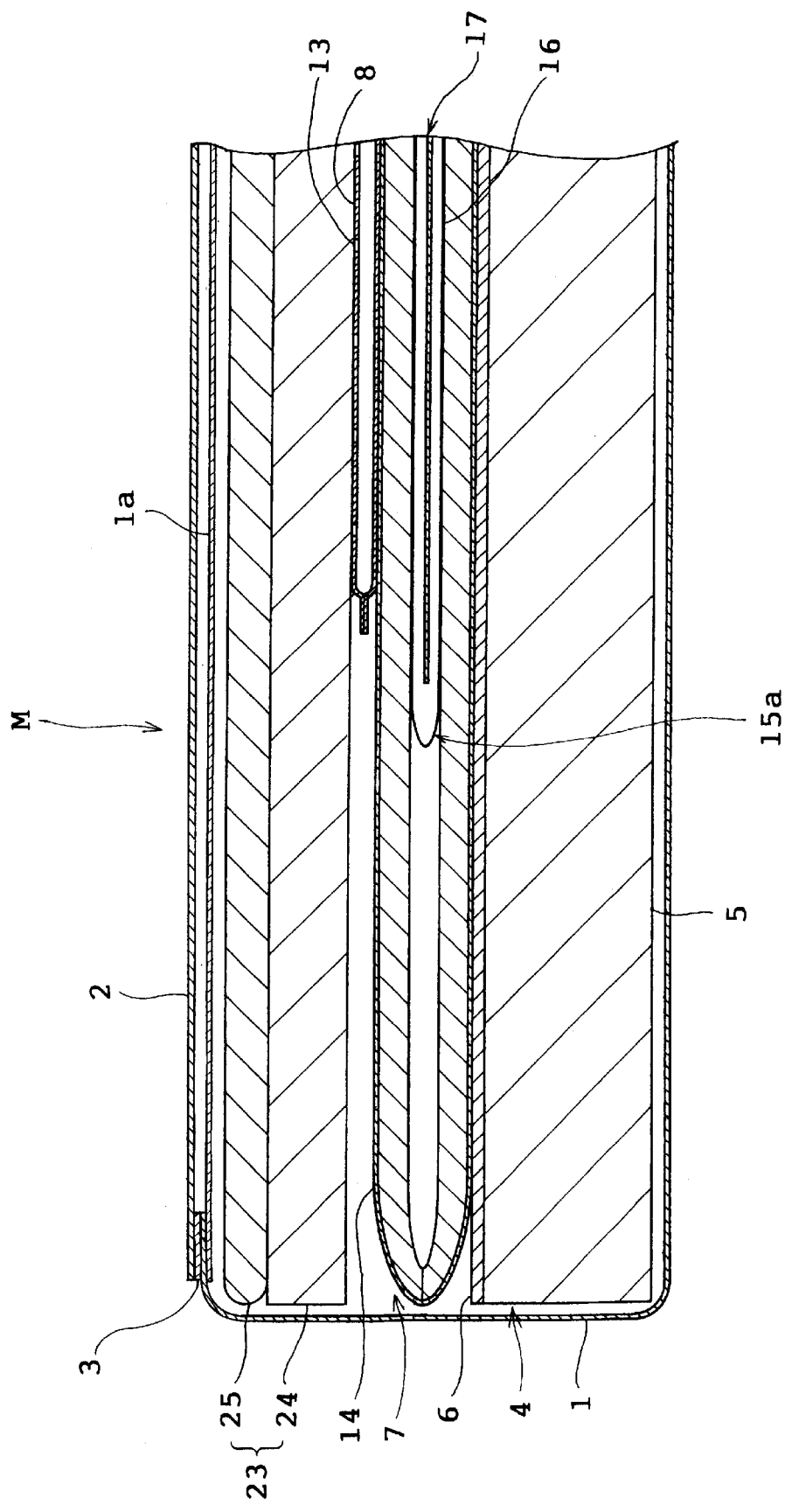
FIG. 1 is a partial longitudinal side section of a mattress of a first embodiment in accordance with the present invention, the view being taken along line 1—1 in FIG. 2.
Figure 2:
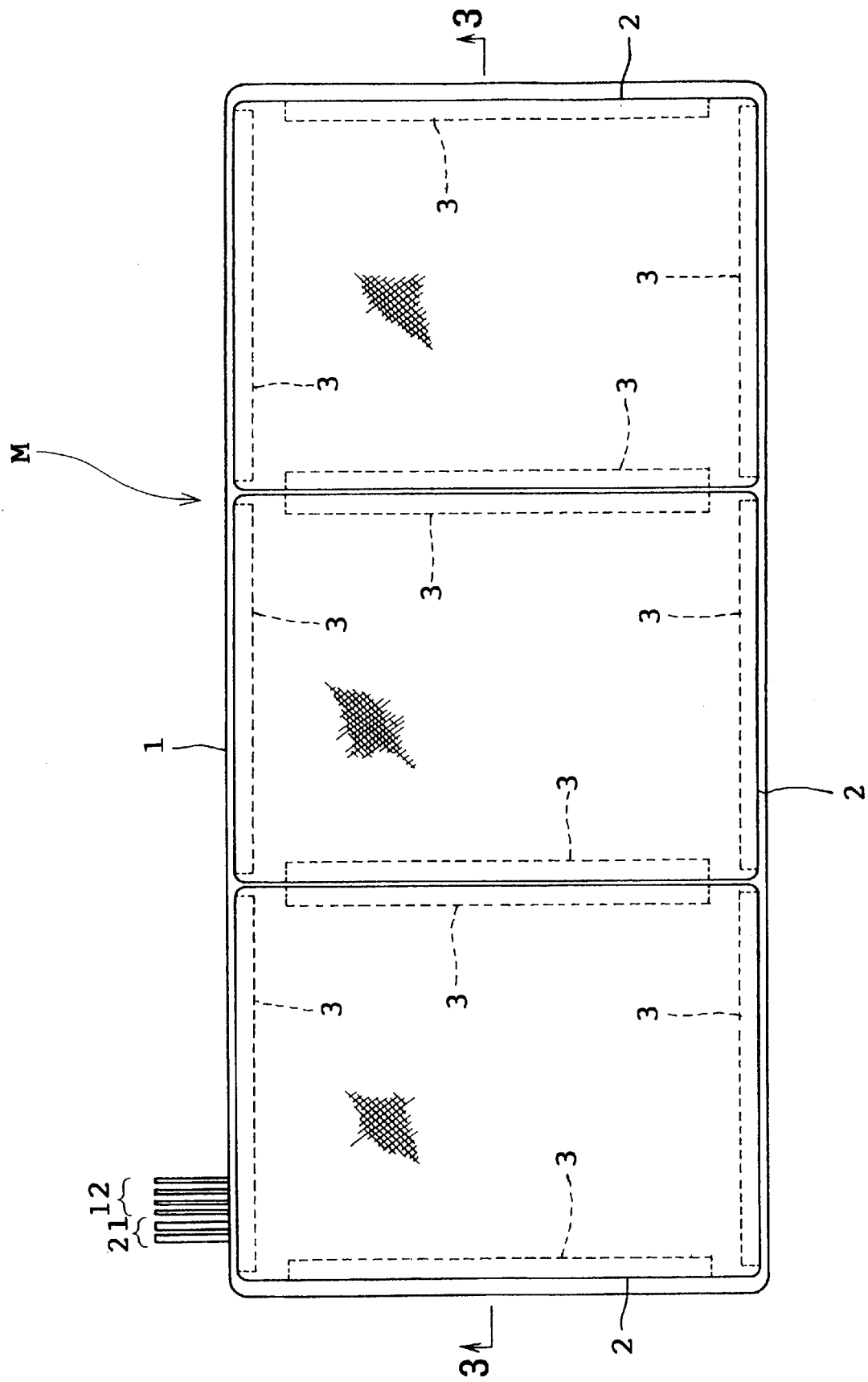
FIG. 2 is a plan view of the mattress.
Figure 3:
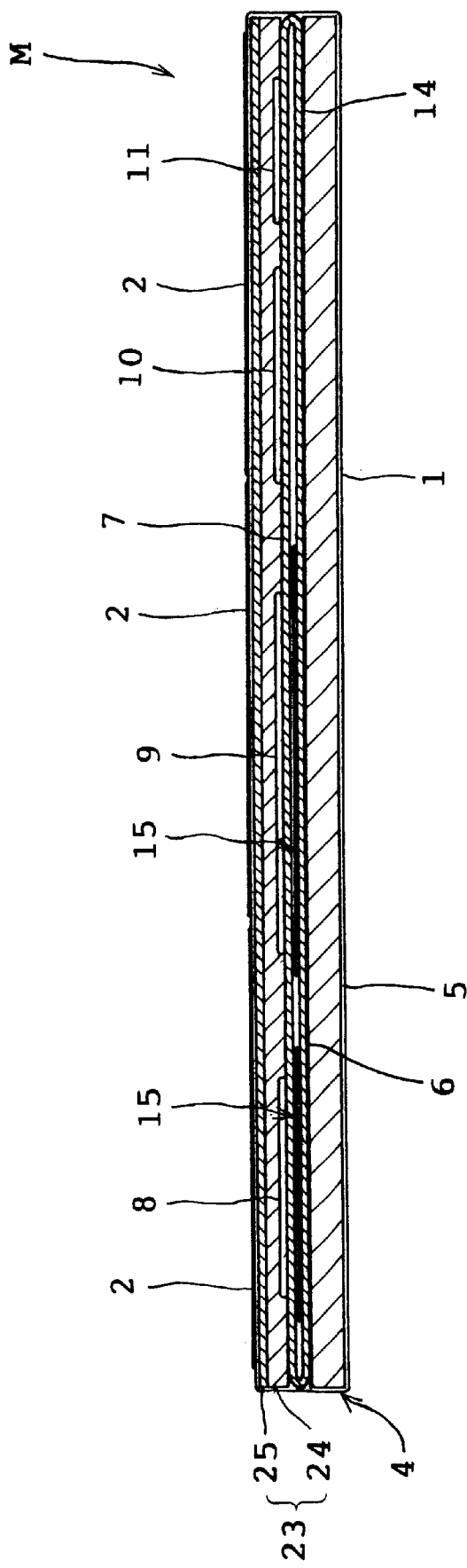
FIG. 3 is a longitudinal section of the mattress taken along line 3—3 in FIG. 2.

The cushion body 23 is formed by stacking a hard cushion 24 made from a synthetic resin and having air permeability and a mat 25 made from a synthetic resin and having air permeability together as shown in FIGS. 1 and 3. The mat 25 is made of a porous material (meshed member) having a superior air permeability to the hard cushion 24. Since the cushion body 23 has a multi-layer structure (two-layer structure in the embodiment), the load of the body of the patient can be dispersed onto the overall cushion 4.

Figure 9:
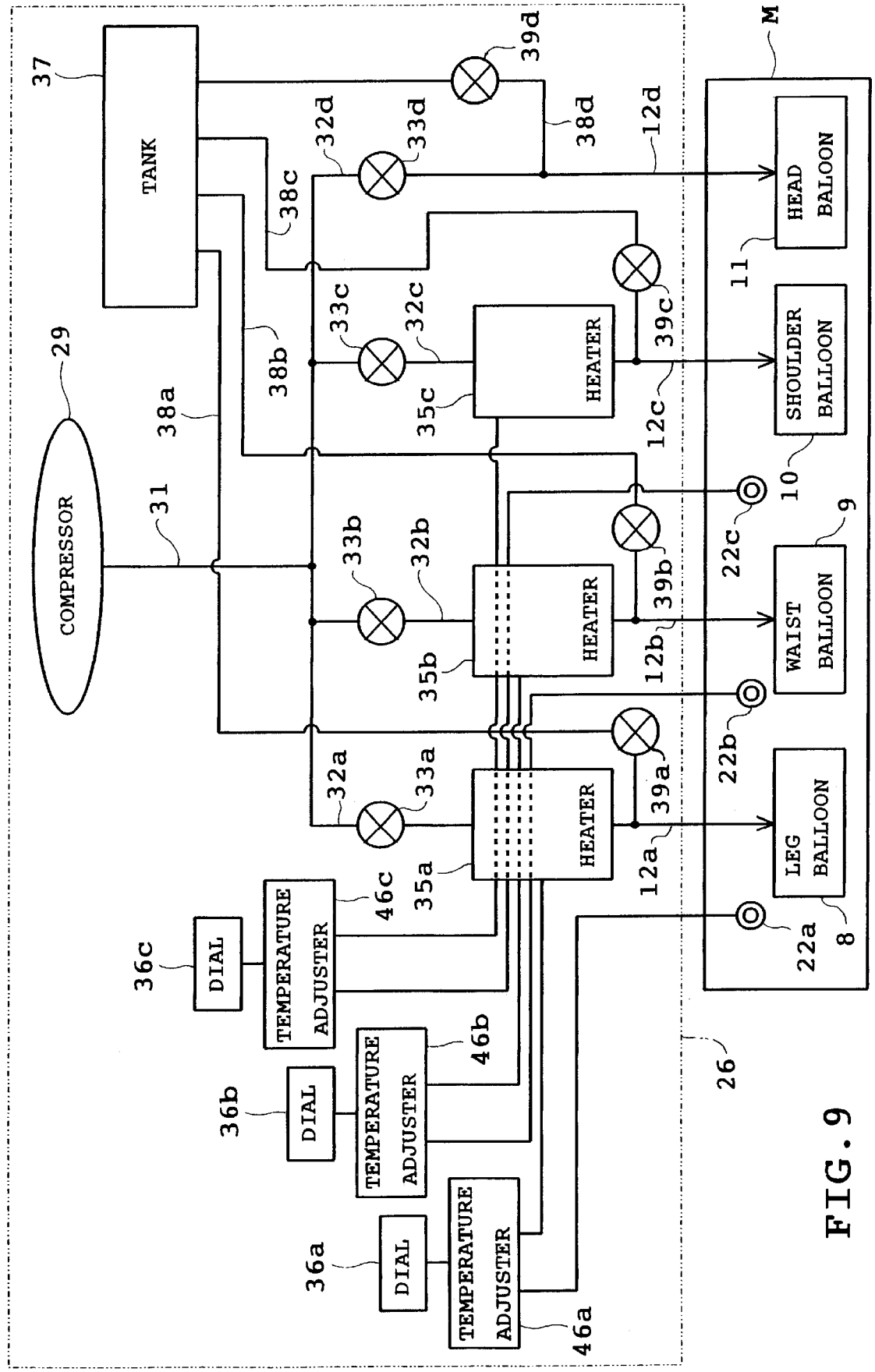
FIG. 9 is a circuit diagram showing an electrical arrangement of one part of the controller.
Figure 10:
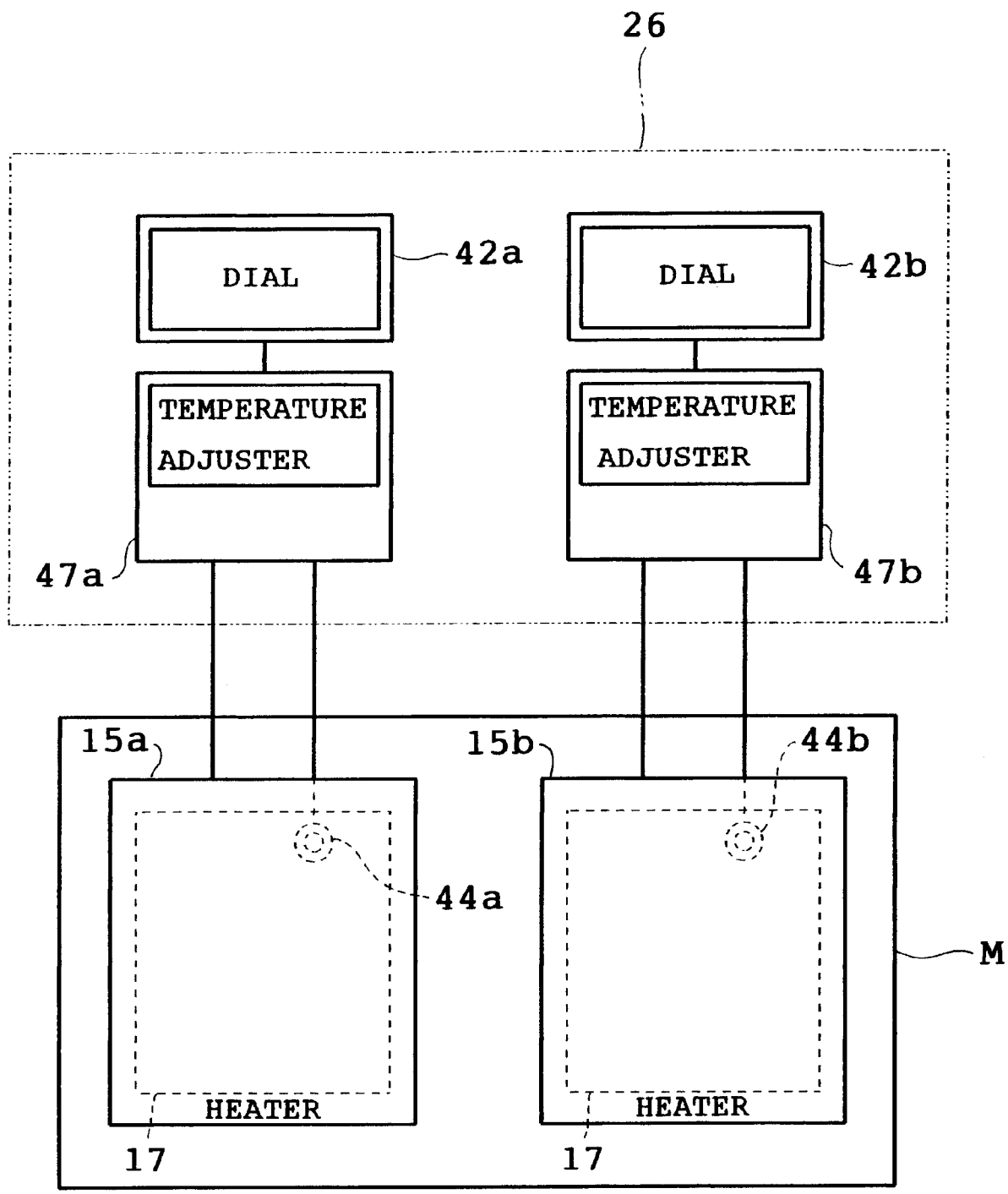
FIG. 10 also a circuit diagram showing an electrical arrangement of another part of the controller.

The controller 26 will now be described with reference to FIGS. 9 and 10 showing an arrangement for the balloons 8 to 11 and an arrangement for the heaters 15a and 15b respectively. A compressor 29 serving as an air supply is provided in the controller 26. Electric power is supplied through the cord 26a to the controller 26. The compressor 29 has a discharge opening to which one end of the air pipe 31 is connected. Ends of the four relay pipes 32a to 32d are connected to the other end of the air pipe 31. The other ends of the relay pipes 32a to 32d are connected to connectors (not shown) in the rear of the controller 26 respectively. A blowing tube 12 includes four tubes 12a to 12d communicating with the balloons 8 to 11 respectively and a covering member covering the tubes. The blowing tube 12 has a connector 45 at one end thereof. The connector 45 is connected to the connectors on the rear of the controller 26. As a result, the relay pipes 32a to 32c are connected to the tubes 12a to 12d respectively. As the result of the above-described construction, air discharged from the discharge opening of the compressor 29 into the air pipe 31 further flows through the relay pipes 32a to 32d and the tubes 12a to 12d into the balloons 8 to 11 to be discharged outward from the discharge holes 13, respectively. Accordingly, the air pipe 31, relay pipes 32a–32d and tubes 12a–12d constitute blowing passages.

Figure 11:
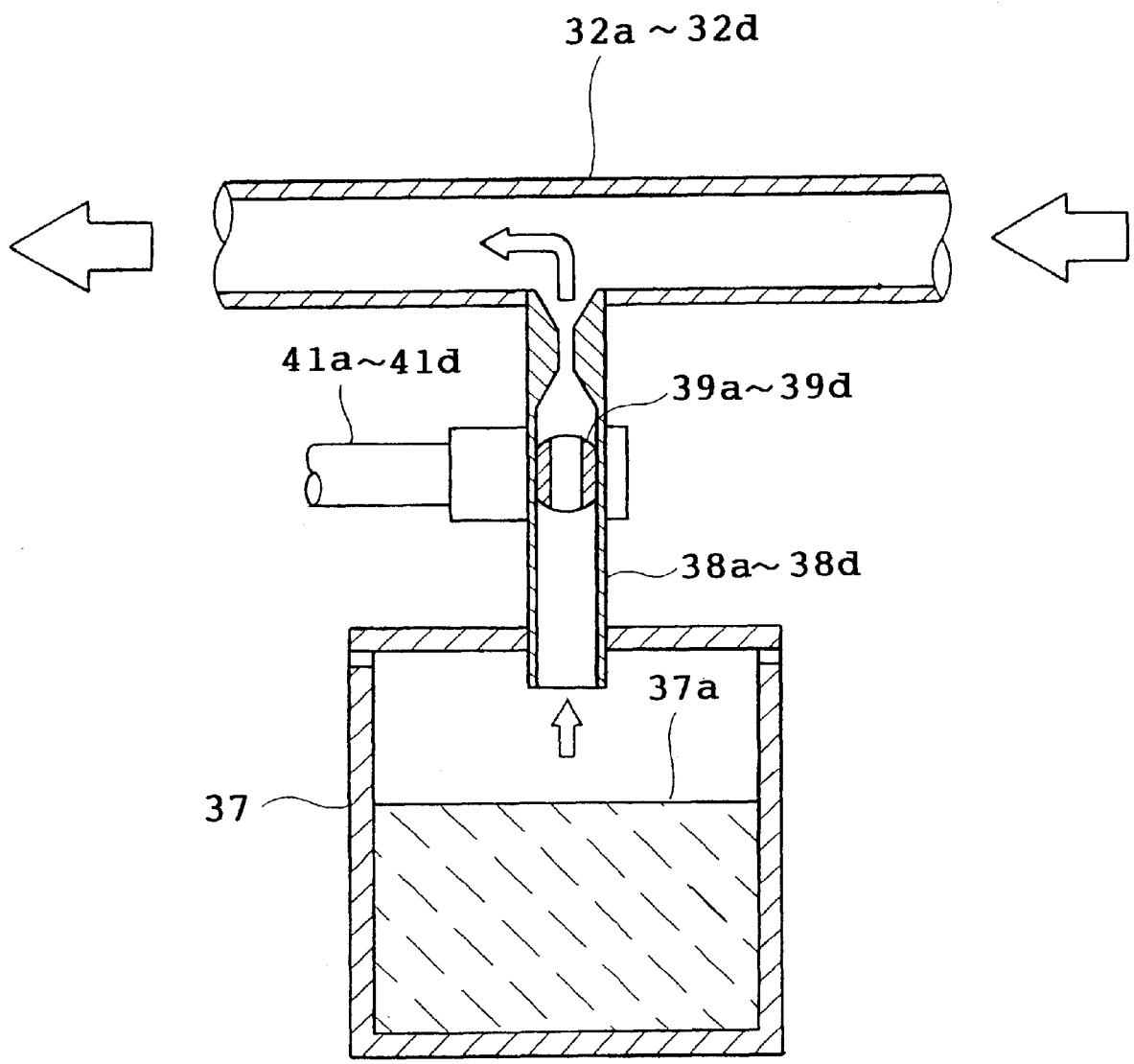
FIG. 11 is a longitudinal section showing a tank containing disinfectant solution and connected via valves to a relay pipe.

Manually operated valves 33a to 33d are provided in the middle of the relay pipes 32a to 32d respectively. Heaters 35a to 35c are provided in the middle of the relay pipes 32a to 32c corresponding to the leg, waist and shoulder balloons 8, 9 and 10 so as to be located downstream with respect to the valve 33, respectively. Each heater comprises a pipe and a heating element such as nichrome wire enclosed in the pipe, for example. A tank 37 is also provided in the controller 26. A predetermined amount of disinfectant solution 37a is reserved in the tank 37 as shown in FIG. 11. Ends of four disinfection pipes 38a to 38d are connected to the top of the tank 37. The other ends of the pipes 38a to 38d are connected to portions of the relay pipes 32a to 32c located downstream with respect to the heaters 35a to 35c respectively as shown in FIG. 9. The other end of the disinfection pipe 35d is connected to a portion of the relay pipe 32d downstream with respect to the valve 33d. Four manually operated valves 39a to 39d are provided in the middle of the disinfection pipes 38a to 38d respectively. When the valves 39a to 39d are opened, gasified disinfectant solution 37a flows through the disinfection pipes 38a to 38d into the relay pipes 32a to 32d respectively. Accordingly, the tank 37 serves as a disinfectant supply.

Four temperature adjusters 46a to 46c are provided in the controller 26 for adjusting temperatures of air discharged from the balloons 8 to 10 by on-off control of the heaters 35a to 35c respectively. Furthermore, two temperature adjusters 47a and 47b are also provided in the controller 26 for adjusting temperatures of the heaters 15a and 15b by on-off control of the heaters respectively as shown in FIG. 10.

Figure 8:
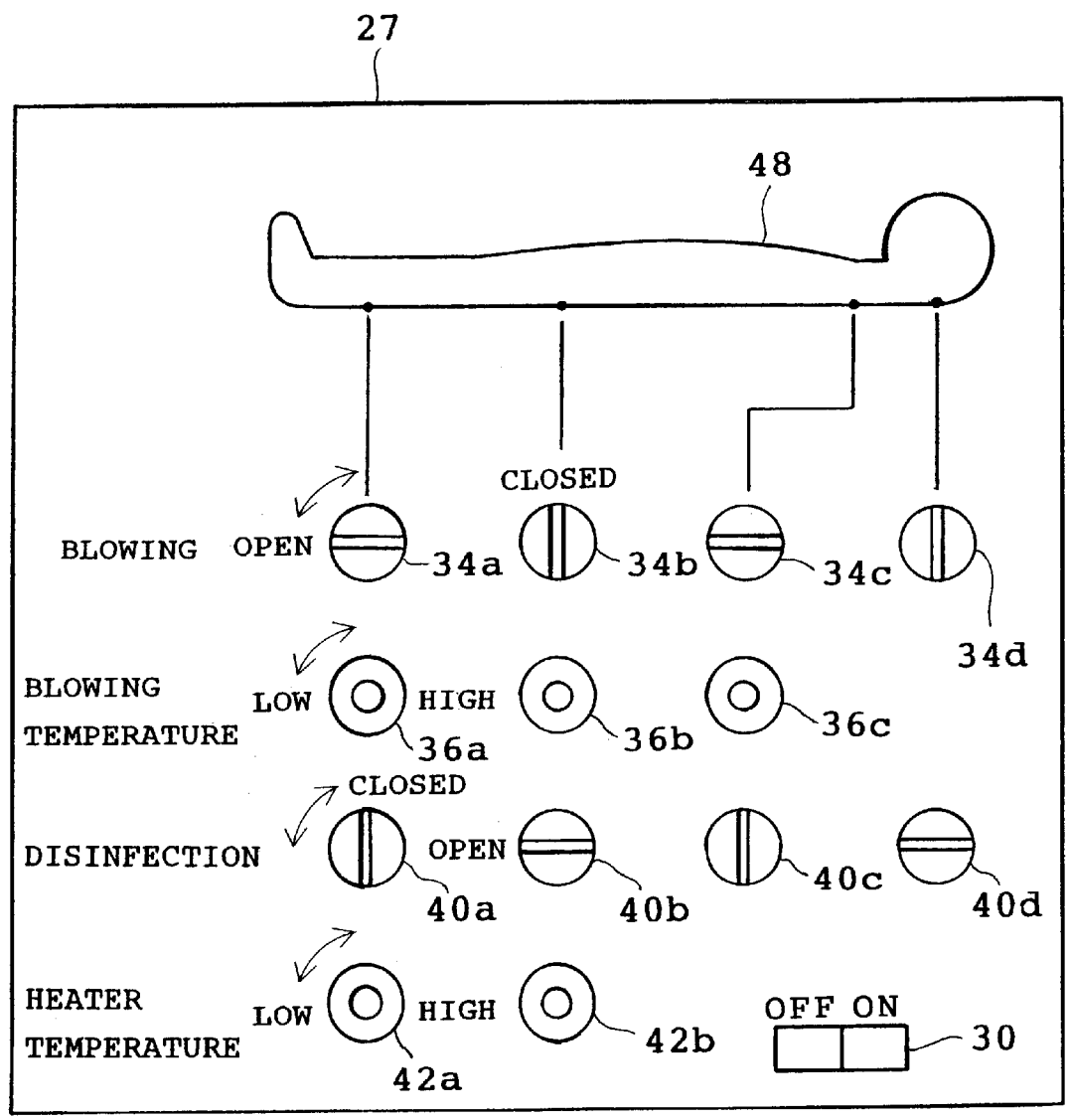
FIG. 8 is a front view of an operation panel of a controller.

The operation panel 27 will now be described with reference to FIG. 8. A power switch 30 is provided on a lower right-hand portion of the operation panel 27. A FIG. 48 representative of a human body is displayed on an upper portion of the operation panel 27. A number of dials serving as operating means are provided below the FIG. 48 on the operation panel 27. More specifically, dials 34a to 34d are provided for setting as to whether air should be discharged from the balloons 8 to 11. The dials 34a to 34d are operatively coupled to valve rods of the valves 33a to 33d so that the valves 33a to 33d are opened and closed when the dials 34a to 34d are operated, respectively. Dial 40a to 40d are provided for setting as to whether the gasified disinfectant solution 37a should be mixed with air discharged from the balloons 8 to 11. The dials 40a to 40d are operatively coupled to valve rods of the valves 39a to 39d so that the valves 39a to 39d are opened and closed when the dials 40a to 40d are operated, respectively.

Dials 36a to 36c are provided for setting temperatures of air discharged from the balloons 8 to 11 respectively. On the basis of set contents of the dials 36a to 36c and temperatures detected by the temperature sensors 22a to 22c, the temperature adjusters 46a to 46c control the heaters 35a to 35c so that the heaters are turned on and off, respectively. Dials 42a and 42b are provided for setting temperatures of the heaters 15a and 15b respectively, on the basis of set temperatures of the dials 42a and 42b and temperatures detected by the temperature sensors 44a and 44b, the temperature adjusters 47a and 47b control the heaters 15a and 15b so that the heaters are turned on and off, respectively.

The dials 34a, 36a, 40a and 42a for the leg balloon 8 and heater 15a are disposed on the operation panel 27 so as to correspond to a leg part of the figure 48. The dials 34b, 36b, 40b and 42b for the waist balloon 9 and heater 15b are disposed on the operation panel 27 so as to correspond to a waist part of the figure 48. The dials 34c, 36c and 40c for the shoulder balloon 10 are disposed on the operation panel 27 so as to correspond to a shoulder part of the figure 48. The head balloon 11 and dials 34d and 40d are disposed on the operation panel 27 so as to correspond to a head part of the figure 48. Accordingly, when viewing the figure 48, the user can confirm correspondence of each dial to a part of the human body. As a result, error in the operation of the dials can be prevented.

The operation of the mattress will now be described. When the power switch 30 is switched to the ON position, the compressor 29 is energized to be driven so that air is discharged from the discharge opening thereof into the air pipe 31. In this state, when the dials 34a to 34d are operated to assume the open positions, the valves 33a to 33d are opened, respectively. As a result, air in the air pipe 31 flows through the relay pipes 32a to 32d and air tubes 12a to 12d into the balloons 8 to 11, respectively. Air flowed into the balloons 8 to 11 is discharged upward from the discharge holes 13. Since the hard cushion 24 and mat 25 disposed over the balloons 8 to 11 are made of the porous material, the air discharged from the balloons 8 to 11 readily passes through the cushion 24 and mat 25. The air having passed through the cushion 24 and mat 25 further passes through the cloth 1a and sheet 2, blowing over the mattress M.

The dials 34a to 34d are operable independent of one another and accordingly, air can be discharged from the balloons 8 to 11 independent of one another. In this case, when the dials 40a to 40d are operated so as to assume open positions, the valves 39a to 39d are opened, respectively. Consequently, gasified disinfectant solution 37a in the tank 37 flows through the pipes 38a to 38d into the relay pipes 32a to 32d. Accordingly, the air discharged from the balloons 8 to 11 is mixed with the gasified disinfectant solution 37a. Since the dials 40a to 40d are operable independent of one another, it can be determined according to the conditions of parts whether the air discharged from the balloons 8 to 11 should be mixed with the gasified disinfectant solution 37a.

Furthermore, the heaters 35a to 35c are energized when the dials 36a to 36c are turned from the respective OFF positions so that temperatures of blown air are set. As a result, air passing through the relay pipes 32a to 32d is heated by the heaters 35a to 35c, respectively. Further, the temperature adjusters 46a to 46c control energization to the heaters 35a to 35c on the basis of the temperatures set by the dials 36a to 36c and temperatures detected by the temperature sensors 22a to 22c, respectively. Accordingly, air discharged from the balloons 8 to 11 has temperatures according to those set by the dials 36a to 36c, respectively. Additionally, since the dials 36a to 36c are operable independent of one another, temperatures of air discharged from the balloons 8 to 11 can be set independent of one another.

On the other hand, the heaters 15a and 15b are energized when the dials 42a and 42b are turned from the respective OFF position so that heater temperatures are set, respectively. The filament 20 generates heat such that far infrared radiation is caused. Further, the temperature adjusters 47a and 47b control energization to the heaters 15a and 15b on the basis of the set temperatures of the dials 42a and 42b and temperatures detected by the temperature sensors 44a and 44b respectively. The dials 42a and 42b are operable independent of each other. Accordingly, the heaters 15a and 15b are operable independent of each other as to whether they should be energized. The heaters 15a and 15b are also operable independent of each other when they are set at respective temperatures.

According to the above-described mattress, the heaters 15a and 15b are provided below the cushion body 23 so that far infrared radiation is effected onto the legs and waist of a person lying on the mattress M. Consequently, since the circulation of the blood of the person is facilitated, occurrence and progress of lumbago and arthralgia can be prevented. Further, each of the heaters 15a and 15b comprises the cloth-like heating element 17 having a small thickness. Accordingly, sleep is not disturbed even when the heaters 15a and 15b are disposed inside the mattress M. Moreover, since the heating element 17 spreads over the areas of the mattress M corresponding to the legs and waist of the person lying on the mattress. Consequently, a uniform far infrared radiation can be effected onto the legs and waist.

Further, the balloons 8 to 11 are provided under the cushion body 23 so that air discharged from the balloons are blown against the legs, waist, shoulders and head of the person. Consequently, since the skin of the person is dried, occurrence and progress of bedsore can be prevented. Additionally, gasified disinfectant solution 37a is selectively mixed with air discharged from the balloons 8 to 11. The occurrence and progress of bedsore can further be prevented since this construction prevents pyogenic bacteria from propagation on an affected part of bedsore in the leg, waist, shoulder or head of the person. Moreover, suitably humidifying the skin of an affected part is said to be effective as well as drying the skin of the affected part. The affected part is humidified by blowing the air mixed with the gasified disinfectant solution against the affected part. As a result, the occurrence and progress of bed sore can further be prevented.

Hot air is discharged from the balloons 8 to 10 corresponding to the legs, waist and shoulders respectively. Consequently, since cutaneous respiration is facilitated, the occurrence and progress of bedsore can further be prevented. Further, the balloons 8 to 11 and the heaters 15a and 15b have flexibility. Accordingly, even when the mattress M is bent, air can be discharged from the balloons 8 to 11 and far infrared radiation from the heaters 15a and 15b can be effected. Consequently, the mattress M can be used with, for example, a bed for medical treatment with a posture adjusting mechanism, for example. Further, the heaters 15a and 15b are enclosed in the protecting cushion 7. Consequently, failure of the heaters 15a and 15b can be prevented as much as possible since stress applied to the heaters 15a and 15b due to the weight of the person is reduced by the protecting cushion 7.

Figure 12:
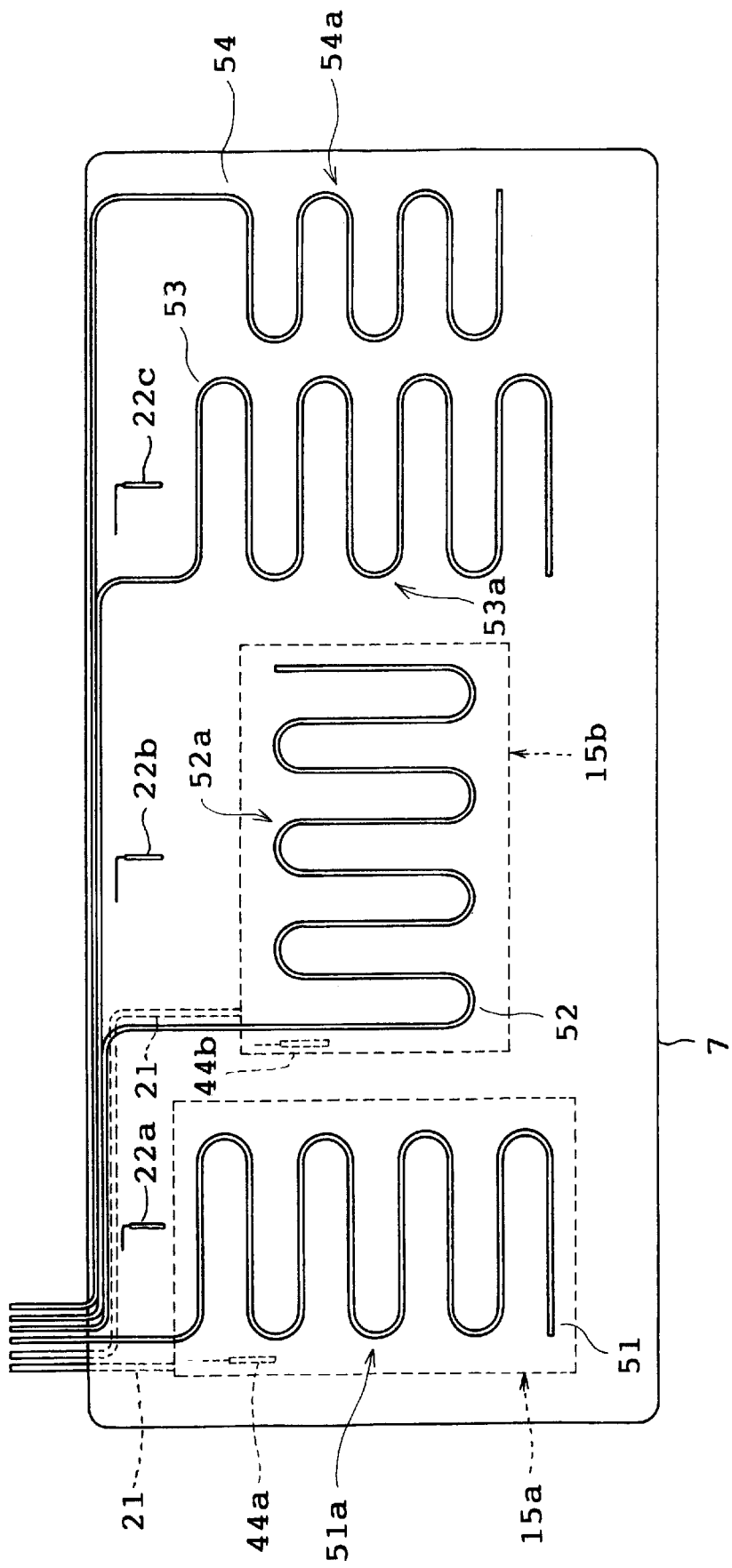
FIG. 12 is a view similar to FIG. 4, showing the mattress of a second embodiment in accordance with the invention.

FIG. 12 illustrates a second embodiment of the invention. only the differences between the first and second embodiments will be described. Identical or similar parts in the second embodiment are labeled by the same reference symbols as those in the first embodiment. In the second embodiment, air tubes 51 to 54 are disposed between the protecting cushion 7 and the cushion body 23, instead of the balloons 8 to 11. Each air tube has flexibility. The air tubes 51 to 54 are bonded to the cover 14 of the protecting cushion 7.

The air tubes 51 to 54 have meandering portions 51a to 54a located below the legs, waist, shoulders and head of the person lying on the mattress M respectively. Each of the meandering portions 51a to 54a is formed with a number of discharge holes (not shown). The connector 45 is provided on the distal ends of portions of the air tubes 51 to 54 located outside the mattress M. The connector 45 is connected to the connector of the controller 26 so that the air tubes 43 to 46 and the relay pipes 32a to 32d are connected to each other respectively.

The other construction of the mattress of the second embodiment is the same as that in the first embodiment. As a result, substantially the same effect can be achieved from the second embodiment as from the first embodiment. Furthermore, as the result of the employment of the air tubes 51 and 52 instead of the balloons 8 and 9, the far infrared radiation from the heaters 15a and 15b can easily reach the legs and waist of the person.

Figure 13:
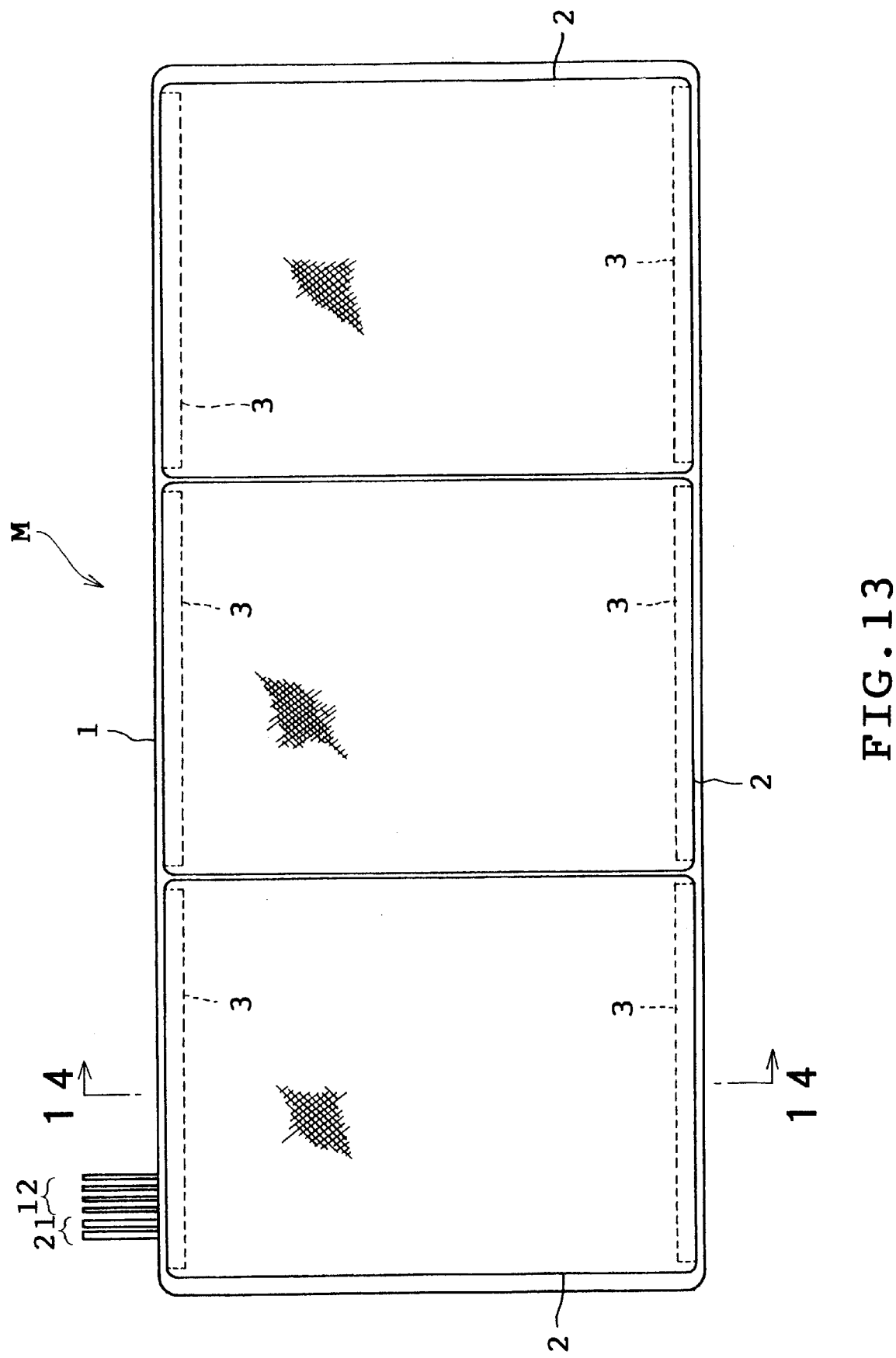
FIG. 13 is a view similar to FIG. 2, showing the mattress of a third embodiment in accordance with the invention.
Figure 14:
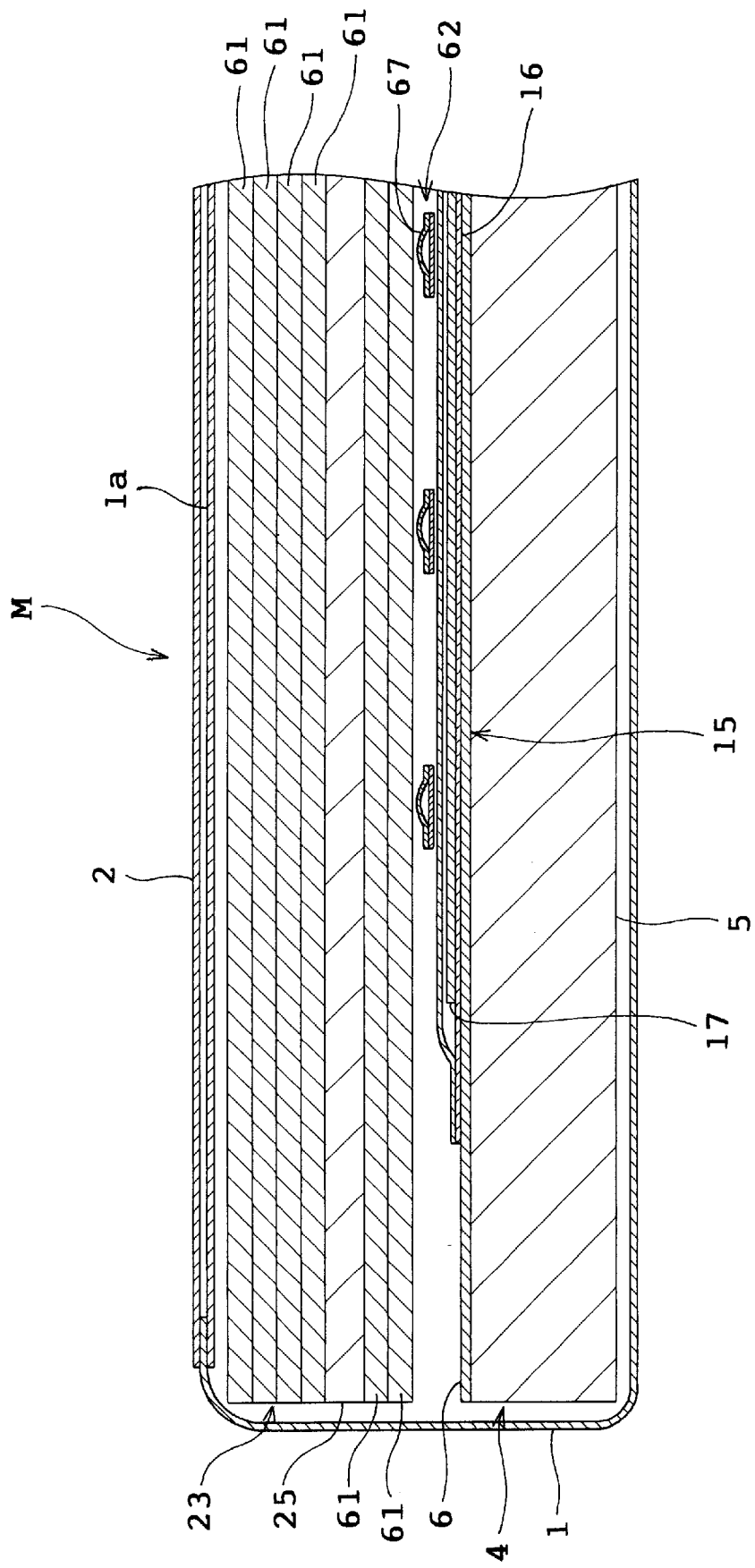
FIG. 14 is a partial longitudinal section taken along line 14—14 in FIG. 13.

FIGS. 13 to 18 illustrate a third embodiment of the invention. Only the differences between the first and third embodiments will be described. In the third embodiment, the sheets 2 are-attached by the sheet fasteners 3 to portions of the mat cover 1 corresponding to both widthwise ends of the mattress M as shown in FIG. 13. Thus, no part of the mattress N on which the person lies includes the sheet fasteners 3. This facilitates sound sleep.

The cushion body 23 includes two flocculent cushions 61, the mat 25 placed on the flocculent cushions, and four flocculent cushions 61 placed on the mat 25. Each flocculent cushion 61 is made of a soft material, for example, a synthetic resin such as polyester. Further, the heaters 15a and 15b are placed directly on the base sheet 6 though they are enclosed in the protecting cushion 7. The heaters 15a and 15b are bonded to an upper side of the base sheet 6.

Two balloons 62 and 63 are disposed on the heaters 15a and 15b, instead of the balloons 8 and 9. The balloons 10 and 11 have the same constructions as those in the first embodiment respectively. The balloon 62 has the same basic construction as the balloon 63. Each of the balloons 62 and 63 is formed by putting upper and lower sheets 64 and 65 each made from vinyl chloride one upon the other and welding peripheral portions of the sheets by high-frequency welding. The lower sheet 65 is wider than the upper sheet 64 and accordingly, both widthwise ends of the balloons 10 and 11 include only the lower sheet. Each of the balloons 62 and 63 has a plurality of openings 66 extending lengthwise and arranged in parallel with one another widthwise with respect to the mattress M. Each opening 66 has a length substantially equal to the width of each of the heaters 15a and 15b. The openings 66 are formed close to the right-hand end of the upper sheet 64 as viewed in FIG. 15. The upper and lower sheets 64 and 65 are welded at peripheral edges of the openings 66 by high-frequency welding.

Figure 15:
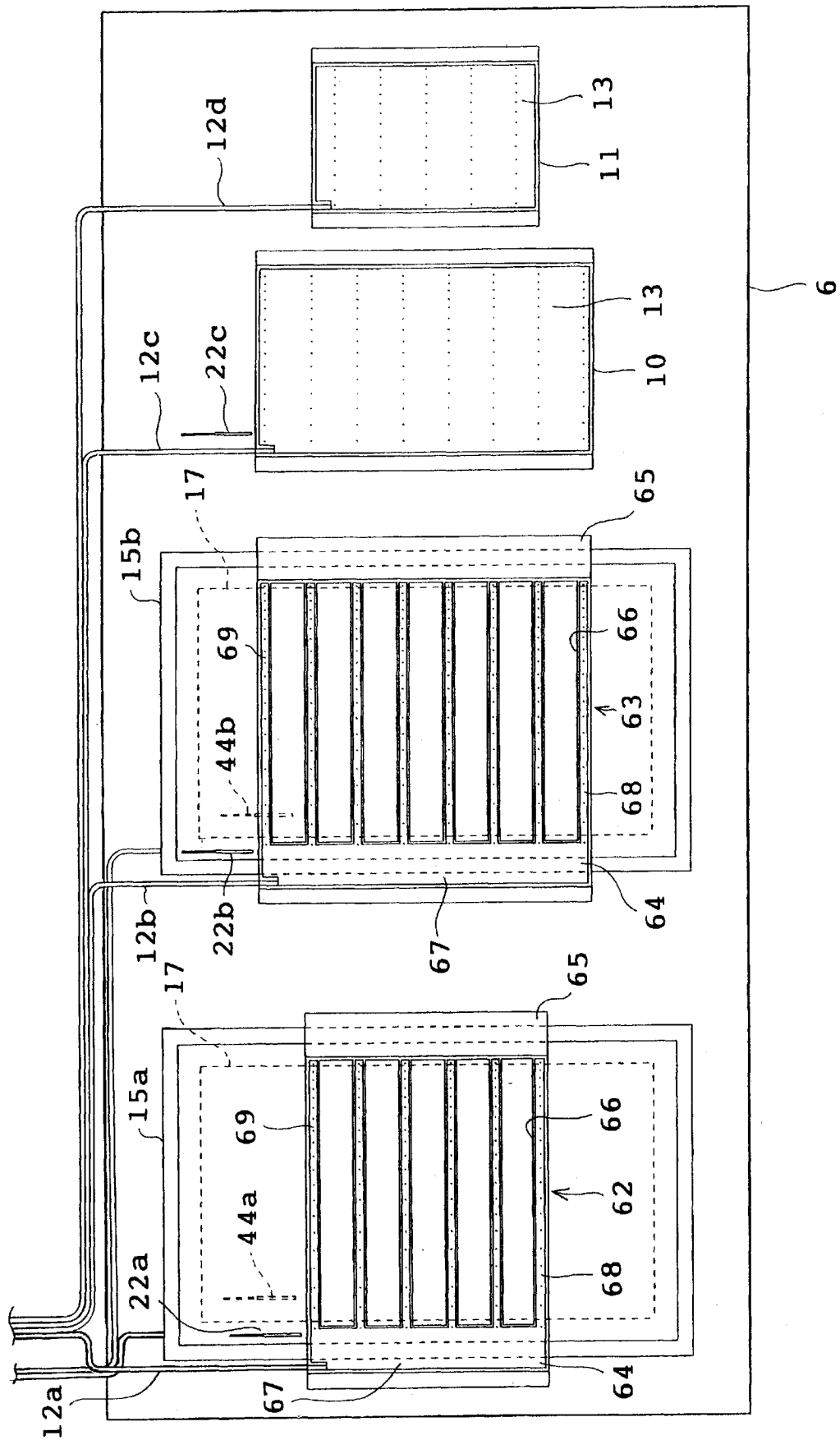
FIG. 15 illustrates arrangement of balloons and heaters on a base sheet.
Figure 16:
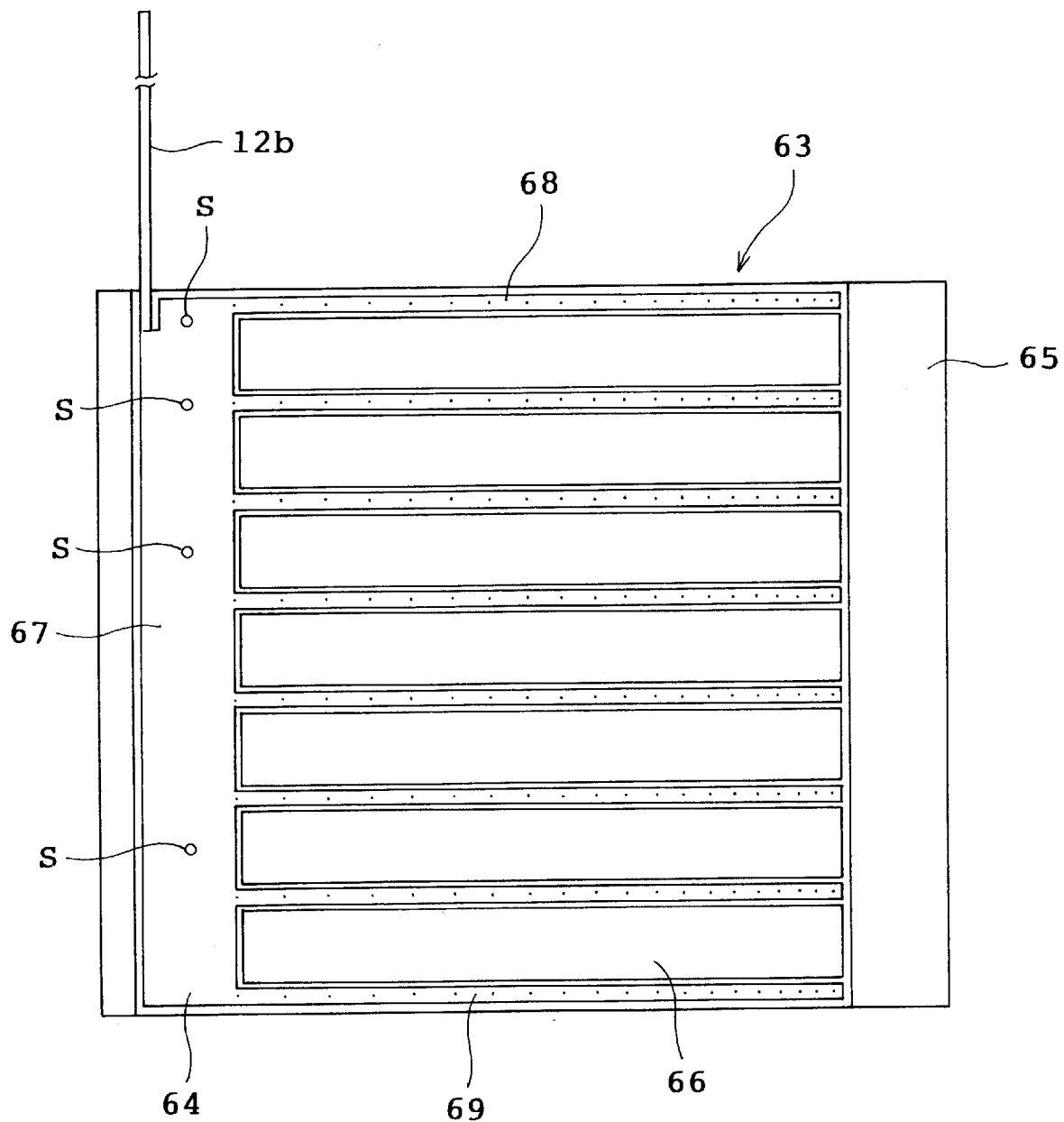
FIG. 16 is a plan view of the balloon.

As a result of the above-described construction, each of the balloons 62 and 63 has a wide air passage 67 formed along the left-hand end of the balloon so as to extend widthwise with respect to the mattress N as viewed in FIG. 15. Each balloon further has a plurality of narrow air passages 68 each extending rightward from the right-hand side of the air passage 67. An air tube 12a is connected to an upper end of the air passage 67 of each balloon as viewed in FIG. 15. The upper and lower sheets 64 and 65 are welded at four points of the air passage 67 by spot welding. In this case, a space S between each weld spot and an adjacent one is increased from the upper end toward the lower end of the air passage 67. Furthermore, each of the air passages 68 has a number of discharge holes 69 formed in the upper side thereof. A space between each hole 69 and an adjacent one is decreased as the hole becomes more distant from the air passage 67. The balloons 62 and 63 are disposed so that the openings 66 are located on the heaters 15a and 15b, respectively.

Figure 17:
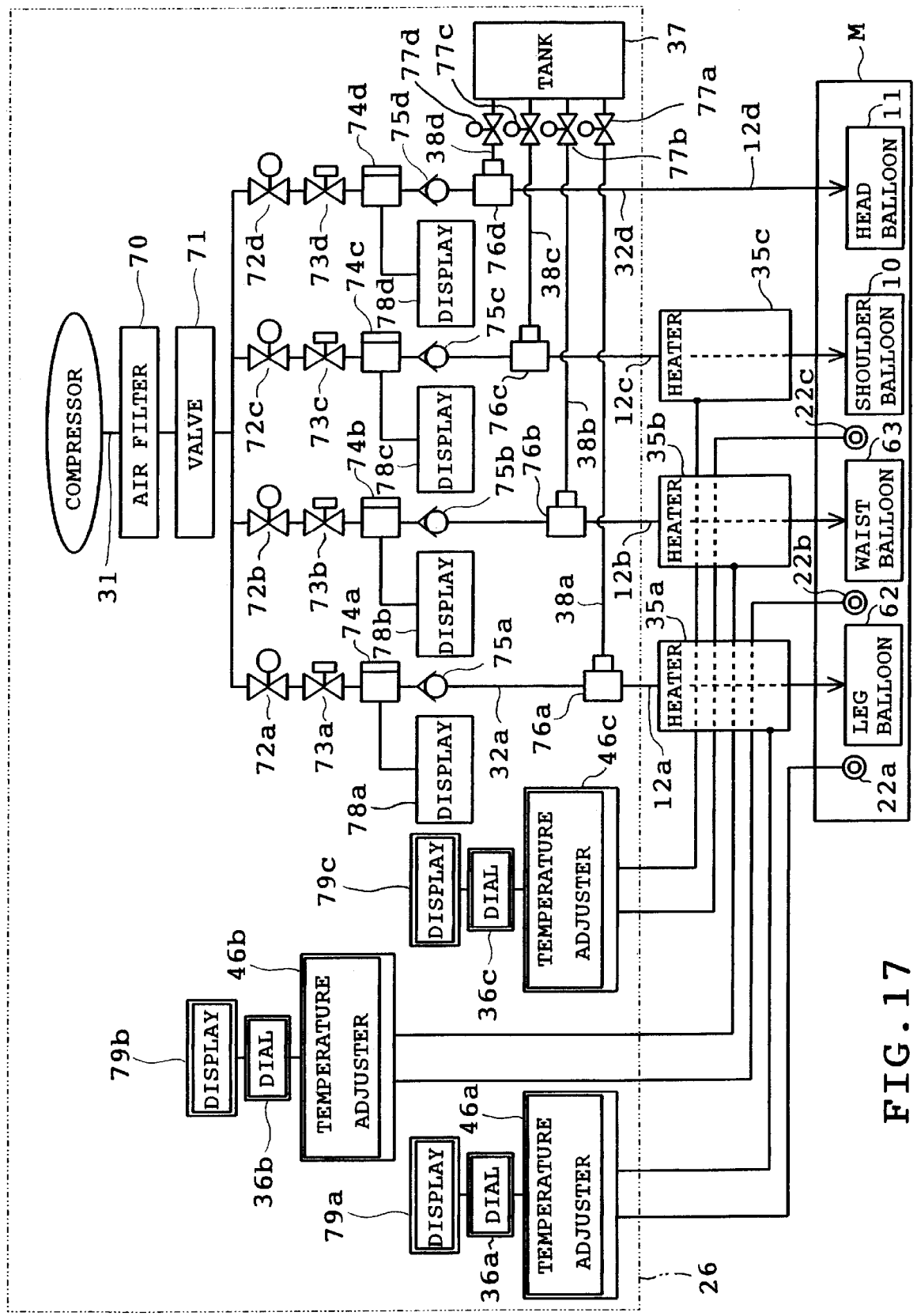
FIG. 17 is a view similar to FIG. 9 in the third embodiment.
Figure 18:
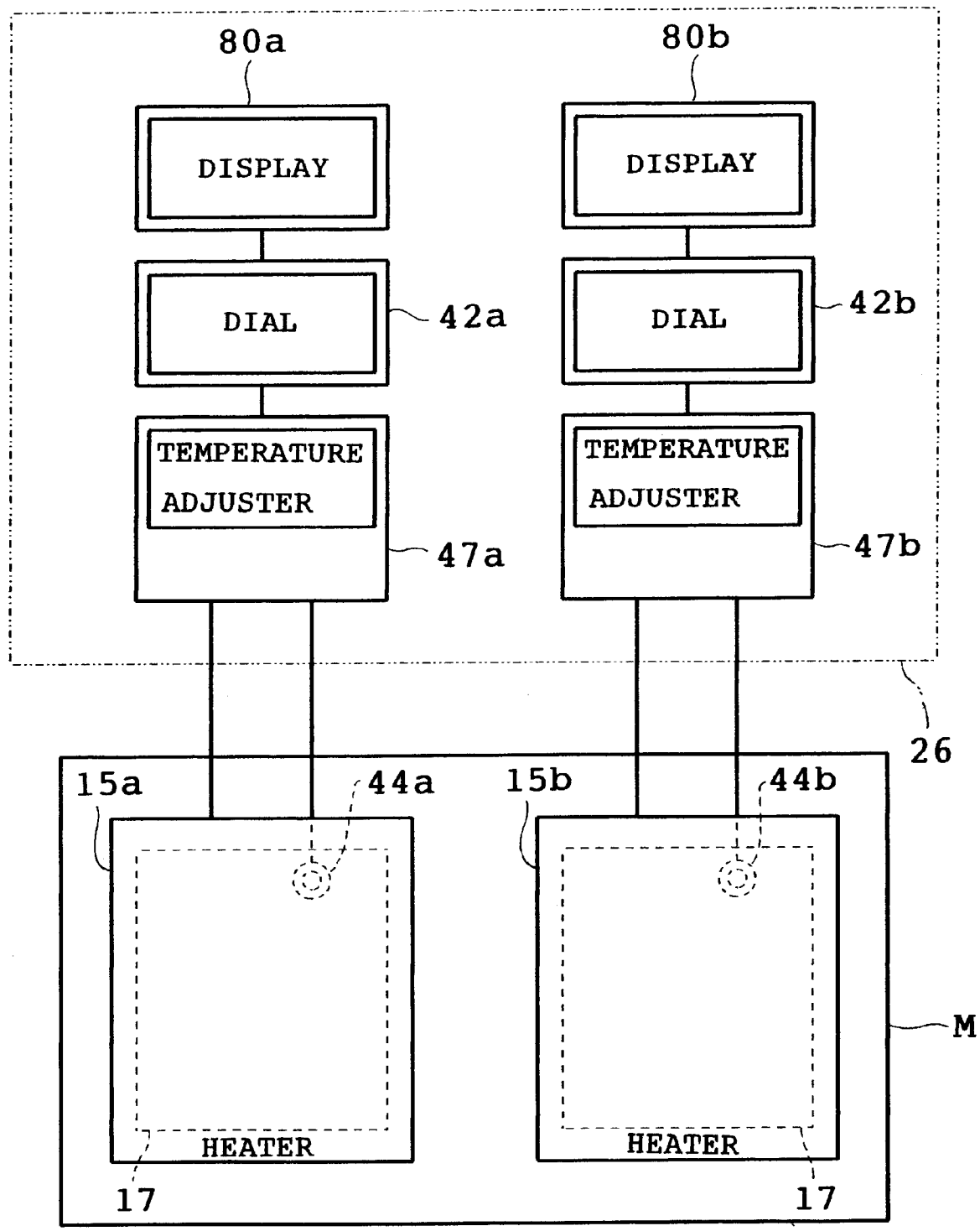
FIG. 18 is a view similar to FIG. 10 in the third embodiment.

The controller 26 will now be described with reference to FIGS. 17 and 18. An air filter 70 and a pressure-regulating valve 71 are provided in the midst of the air pipe 31. The relay pipes 32a to 32d are provided with electromagnetic valves 72a to 72d, needle valves 73a to 73d, flow meters 74a to 74d and check valves 75a to 75d, respectively. In the embodiment, the dials 34a to 34d are connected to valve rods of the needle valves 73a to 73d respectively. Accordingly, amounts of air flowing through the relay pipes 32a to 32d are adjusted when the dials 34a to 34d are turned, respectively. Evacuators 76a to 76d are provided in the junctions between the relay pipes 32a to 32d and the disinfection pipes 38a to 38d respectively. Electromagnetic valves 77a to 77d are provided in the midst of the disinfection pipes 38a to 38d, instead of the valves 39a to 39d, respectively. The heaters 35a to 35d are provided in the midst of the air tubes 12a to 12d respectively. In other words, the heaters 35a to 35d are located outside the controller 26 in the embodiment.

Four displays 78a to 78d are provided on the operation panel 27 for displaying flow rates detected by the flow meters 74a to 74d in a real-time manner respectively. Three displays 79a to 79c are also provided on the operation panel 27 for displaying temperatures of air discharged from the balloons 62, 63 and 10 respectively. Further, two displays 80a and 80b are provided on the operation panel 27 for displaying the temperatures of the heaters 15a and 15b in the real-time manner respectively. Accordingly, the user can confirm the flow rates and temperatures of air discharged from the balloons 62, 63, 10 and 11, and the temperatures of the heaters 15a and 15b when viewing the respective displays 78a to 78d, 79a to 79c and 80a and 80b.

Switches (not shown) are provided on the operation panel 27 for opening and closing the electromagnetic valves 72a to 72d respectively. Further, switches are also provided on the operation panel 27 for opening and closing the electromagnetic valves 77a to 77d, instead of the dials 40a to 40d, respectively.

According to the above-described mattress of the third embodiment, the balloons 62 and 63 disposed on the heaters 15a and 15b have the openings 66 respectively. Consequently, far infrared radiation from the heaters 15a and 15b can more readily reach the legs and waist of the person lying on the mattress M.

When the balloons 62 and 63 have the respective openings 66, the air passages 67 and 68 become narrow such that air supplied from the air tubes 12a and 12b into the air passage 67 is difficult to flow to the distal ends of the air passages 68. In the embodiment, however, the weld spots S are provided on the air passages 67 so that air in the air passage 67 flows substantially uniformly into the air passages 68. Further, the space between each hole 69 and an adjacent one is decreased as the hole becomes more distant from the air passage 67. As a result, since air flows to the distal ends of the air passages 68, air can uniformly be discharged from the air passages 68. Further, as the result of provision of the weld spots S, the air passages 67 can be prevented from being inflated large when air flows into the balloons 62 and 63, and the thicknesses of the balloons 62 and 63 can be maintained approximately at the same value.

Further, each of the balloons 62 and 63 is made by superposing the two sheets 64 and 65 on each other and welding the peripheral portions of the sheets by high-frequency welding. As a result, the balloons 62 and 63 can be thinned. Accordingly, since the balloons 62 and 63 are not bulky, the person lying on the mattress M is free of a feeling of physical disorder.

The flocculent cushion 61 constitutes the top of the cushion body 23. Consequently, the upper surface of the mattress M feels soft. Further, the cushion body 23 comprises combination of the mat 25 having high air permeability and the flocculent cushion 61. This reduces the force of air discharged from the balloons 62, 63, 10 and 11 to be blown through the cushion body 23 upward. The evacuators 76a to 76d are provided in the junctions between the relay pipes 32a to 32d and the disinfection pipes 38a to 38d respectively. Consequently, the disinfectant solution gasified in the pipes 38a to 38d can efficiently be drawn into the relay pipes 32a to 32d respectively.

Air heated by the heaters 35a to 35d is cooled in the air tubes 12a to 12d when the heaters are provided on the respective relay pipes 32a to 32d in the case where the controller 26 is disposed away from the mattress M, that is, the air tubes 12a to 12d are long. In the embodiment, however, the air tubes 12a to 12d are provided with the heaters 35a to 35d respectively. Consequently, air heated by the heaters 35a to 35d can be prevented from being cooled until it is discharged from the balloons 62, 63, 10 and 11. The other construction in the third embodiment is the same as that in the first embodiment and accordingly, the same effect can be achieved from the third embodiment as from the first embodiment.

Figure 19:
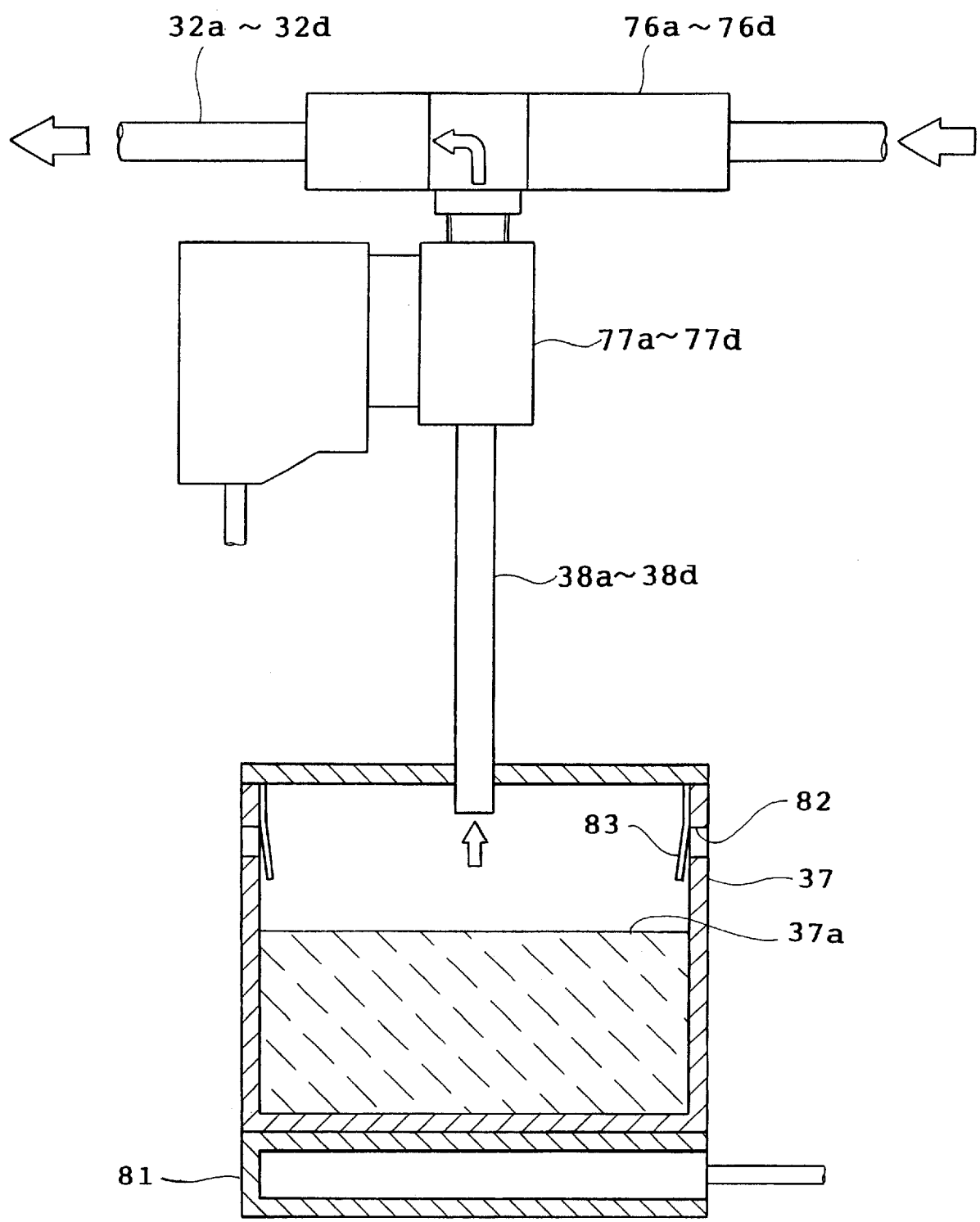
FIG. 19 is a longitudinal section showing a tank containing disinfectant solution and connected via valves to relay pipes.

FIG. 19 illustrates a fourth embodiment of the invention. Only the difference between the third and fourth embodiments will be described. In the fourth embodiment, a heater 81 is provided under the tank 37. The tank 37 has an air hole 82 formed in an upper portion of a side wall thereof. A check valve 82 is mounted on an inner face of the side wall so as to cover the air hole 82. The disinfectant solution 37a reserved in the tank 37 can be heated by the heater 81 to be gasified. Further, the gasified disinfectant solution 37a can efficiently be mixed with air passing through the relay pipes 32a to 32d.

The air discharger includes the leg air discharger, waist air discharger, shoulder air discharger and head air discharger. However, the air discharger may include a single air discharger for the legs and waist and another single air discharger for shoulders and head. Additionally, a single air discharger may be provided for the overall human body. Further, the base mat 5 may have a multi-layer structure. The blowing source may comprise a fan, instead of the compressor.

The cushion body 23 includes the two flocculent cushions 61, the mat 25 placed on the flocculent cushions, and the four flocculent cushions 61 placed on the mat 25 in the third embodiment. However, the flocculent cushion 61 may or may not be disposed under the mat 25. Further, one, five or more flocculent cushions 61 may be disposed on the upper face of the mat 25. In other words, the number of the flocculent cushions 61 disposed on the top and the underside of the mat 25 may be adjusted so that the force of air passing through the cushion body 23 can be adjusted suitably.

Temperature sensors may be provided for detecting temperatures of the heaters 35a to 35c in order that the temperatures of the heaters may be prevented from an abnormal increase. As a result, abnormal conditions of the heaters 35a to 35c can be detected quickly and accordingly, the safety of the mattress can be improved. The operating means for setting the temperatures of the heaters 15a and 15b should not be limited to the rotatable dials. Slidable knobs may be provided instead of the dials. One, two or four sheets 2 may be attached to the upper face of the mat cover 1. Each temperature sensor may comprise a thermopile or thermocouple, instead of the thermistor.

The foregoing description and drawings are merely illustrative of the principles of the present invention and are not to be construed in a limiting sense, various changes and modifications will become apparent to those of ordinary skill in the art. All such changes and modifications are seen to fall within the scope of the invention as defined by the appended claims.

We claim:

1. A mattress comprising:
   a cushion body having air permeability;
   an air discharger provided below the cushion body for discharging air into the cushion body, air discharger having flexibility; and
   a heat source provided below the cushion body for providing far infrared radiation into the cushion body, the heat source having flexibility.

2. A mattress according to claim 1, wherein the heat source comprises a generally cloth-like heat generator made of a filament yarn further made of a synthetic resin with carbon added and a metallic yarn causing the filament yarn to generate heat by means of resistance when the filament yarn is energized.

3. A mattress according to claim 1, further comprising a protecting cushion for accommodating the heat source therein to thereby protect the same.

4. A mattress according to claim 1, further comprising an air supply for supplying air to the air discharger, an air passage connected to the air supply and the air discharger so that air is supplied from the air supply to the air discharger therethrough, and a disinfectant supply for supplying a disinfectant component into the air supplied from the air supply so that the air discharged from the air discharger contains the disinfectant component.

5. A mattress according to claim 1, further comprising an air supply for supplying air to the air discharger, an air passage connected to the air supply and the air discharger so that air is supplied from the air supply to the air discharger therethrough, and a heater provided in the middle of the air passage for heating the air flowing through the air passage.

6. A mattress according to claim 5, wherein the air discharger includes an air discharger for a leg, an air discharger for a waist, an air discharger for a shoulder, and an air discharger for a head, the air passage includes an air passage through which the air is supplied to the air discharger for the leg, an air passage through which the air is supplied to the air discharger for the waist and an air passage through which the air is supplied to the air discharger for the shoulder, and the heater includes a heater for a leg, a heater for a waist and a heater for a shoulder, all of which are provided in the middle of the respective air passages.

7. A mattress according to claim 6, further comprising a controller for controlling the air dischargers for the leg, waist, shoulder, and head respectively independent of one another.

8. A mattress according to claim 7, wherein the controller further controls the heaters for the leg, waist and shoulder respectively independent of one another.

9. A mattress according to claim 1, further comprising an air supply for supplying air to the air discharger, an air passage connected to the air supply and the air discharger so that air is supplied from the air supply to the air discharger therethrough, and a disinfectant supply provided in the middle of the air passage for supplying a disinfectant component into the air supplied from the air supply so that the air discharged from the air discharger contains the disinfectant component.

10. A mattress according to claim 1, further comprising a covering member for covering the cushion body, the air discharger and the heat source, the covering member having an upper side formed with a number of air holes, and a sheet detachably attached to the upper side of the covering member so as to cover the air holes of the covering member, the sheet having air permeability.

11. A mattress according to claim 1, wherein the heat source includes a heat source for a leg and a heat source for a waist.

12. A mattress according to claim 11, further comprising a controller for controlling the heat sources for the leg and waist independently of each other.

13. A mattress according to claim 1, wherein the air discharger includes an air discharger for a leg, an air discharger for a waist, an air discharger for a shoulder, and an air discharger for a head.

14. A mattress according to claim 13, further comprising a controller for controlling the air dischargers for the leg, waist, shoulder, and head respectively independent of one another.

15. A mattress according to claim 1, wherein the cushion body includes a cushiony flocculent cushion and a porous member having air permeability, the flocculent cushion and the porous member being superimposed on each other.

16. A mattress according to claim 1, wherein the heat source is disposed below the air discharger and the air discharger has a number of openings through which the far infrared radiation from the heat source passes.

17. A mattress according to claim 1, further comprising a base mat over which the air discharger and the heat source are disposed.

* * * * *